(12) United States Patent
Leak et al.

(10) Patent No.: US 9,707,351 B2
(45) Date of Patent: Jul. 18, 2017

(54) DOSE SETTING MECHANISM AND METHOD OF USING SAME

(75) Inventors: David Martin Leak, Lake Hopatcong, NJ (US); Joseph Butler, Warwickshire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 267 days.

(21) Appl. No.: 13/878,463

(22) PCT Filed: Oct. 11, 2011

(86) PCT No.: PCT/EP2011/067677
§ 371 (c)(1),
(2), (4) Date: Apr. 9, 2013

(87) PCT Pub. No.: WO2012/049140
PCT Pub. Date: Apr. 19, 2012

(65) Prior Publication Data
US 2013/0197478 A1  Aug. 1, 2013

Related U.S. Application Data

(60) Provisional application No. 61/392,749, filed on Oct. 13, 2010.

(30) Foreign Application Priority Data

May 31, 2011 (EP) .................................... 11168189

(51) Int. Cl.
*A61M 5/315* (2006.01)

(52) U.S. Cl.
CPC .... *A61M 5/31528* (2013.01); *A61M 5/31525* (2013.01); *A61M 5/31538* (2013.01);
(Continued)

(58) Field of Classification Search
CPC ............ A61M 5/31595; A61M 5/3158; A61M 5/31563; A61M 5/31551; A61M 5/31536; A61M 5/31535; A61M 5/31528
(Continued)

(56) References Cited

U.S. PATENT DOCUMENTS

| 5,092,842 A | 3/1992 | Bechtold et al. |
| 5,626,566 A * | 5/1997 | Petersen et al. ............... 604/208 |

(Continued)

FOREIGN PATENT DOCUMENTS

| WO | 2004/020027 | 3/2004 |
| WO | 2004/078239 | 9/2004 |

OTHER PUBLICATIONS

International Search Report and Written Opinion for International App. No. PCT/EP2011/067677, mailed Mar. 2, 2012.

(Continued)

*Primary Examiner* — Nathan R Price
*Assistant Examiner* — Weng Lee
(74) *Attorney, Agent, or Firm* — McDonnell Boehnen Hulbert & Berghoff LLP (57) ABSTRACT

The present invention relates to a dose setting mechanism for a drug delivery device and a method of using same. The mechanism comprises a drug delivery device housing, a dose dial sleeve positioned at least partly in the housing and being rotatable during dose setting and dose delivery, a clutch rotatable during dose setting and non-rotatable during dose delivery, and a clutch nut, that is threadedly engaged with the clutch and is splined to the housing to prevent rotation of the clutch nut.

10 Claims, 5 Drawing Sheets

(52) U.S. Cl.
CPC .... *A61M 5/31551* (2013.01); *A61M 5/31585* (2013.01); *A61M 5/31571* (2013.01)

(58) Field of Classification Search
USPC .......................... 604/150–157, 238, 66, 122
See application file for complete search history.

(56) References Cited

U.S. PATENT DOCUMENTS

| | | | |
|---|---|---|---|
| 2005/0033224 A1 | 2/2005 | Kirchhofer et al. | |
| 2008/0287883 A1* | 11/2008 | Radmer et al. | 604/211 |
| 2009/0198193 A1* | 8/2009 | Veasey et al. | 604/207 |
| 2009/0264828 A1* | 10/2009 | Dette | A61M 5/31533 604/189 |
| 2009/0275916 A1* | 11/2009 | Harms et al. | 604/506 |

OTHER PUBLICATIONS

International Preliminary Report on Patentability for International App. No. PCT/EP2011/067677, mailed Feb. 21, 2013.
Written Opinion of the International Preliminary Examining Authority for International App. No. PCT/EP2011/067677, mailed Dec. 17, 2012.

* cited by examiner

Table 1

| Dialed Insulin Dose | Pen Number | | | |
|---|---|---|---|---|
| | 1 | 2 | 3 | 4 |
| 2 | ░ | ░ | ░ | ░ |
| 4 | ░ | ░ | ░ | ░ |
| 6 | ░ | ░ | ░ | ░ |
| 8 | ░ | ░ | ░ | ░ |
| 10 | ▞ | ░ | ░ | ░ |
| 12 | ▞ | ░ | ░ | ░ |
| 14 | ▞ | ░ | ░ | ░ |
| 16 | ▞ | ░ | ░ | ░ |
| 18 | ▞ | ▞ | ░ | ░ |
| 20 | ▞ | ▞ | ░ | ░ |
| 22 | ▞ | ▞ | ░ | ░ |
| 24 | | ▞ | ░ | ░ |
| 26 | | ▞ | ░ | ░ |
| 28 | | ▞ | ░ | ░ |
| 30 | | ▞ | ░ | ░ |
| 32 | | ▞ | ░ | ░ |
| 34 | | ▞ | ░ | ░ |
| 36 | | ▞ | ░ | ░ |
| 38 | | ▞ | ▞ | ░ |
| 40 | | ▞ | ▞ | ░ |
| 42 | | ▞ | ▞ | ░ |
| 44 | | | ▞ | ░ |
| 46 | | | ▞ | ░ |
| 48 | | | ▞ | ░ |
| 50 | | | ▞ | ░ |
| 52 | | | ▞ | ░ |
| 54 | | | ▞ | ░ |
| 56 | | | ▞ | ░ |
| 58 | | | ▞ | ▞ |
| 60 | | | ▞ | ▞ |
| 62 | | | ▞ | ▞ |
| 64 | | | | ▞ |
| 66 | | | | ▞ |
| 68 | | | | ▞ |
| 70 | | | | ▞ |
| 72 | | | | ▞ |
| 74 | | | | ▞ |
| 76 | | | | ▞ |
| 78 | | | | ▞ |
| 80 | | | | ▞ |

▞ Dose may be dialed and delivered
░ Low dose - Cannot be dispensed
☐ High dose - Cannot be dialed

FIG. 6

| Table 2 Dialed Insulin Dose | Pen Number 1 | 2 | 3 | 4 |
|---|---|---|---|---|
| 2 | ← | ← | ← | ← |
| 4 | ← | ← | ← | ← |
| 6 | ← | ← | ← | ← |
| 8 | ← | ← | ← | ← |
| 10 | ✓ | ← | ← | ← |
| 12 | ✓ | ← | ← | ← |
| 14 | ✓ | ← | ← | ← |
| 16 | ✓ | ← | ← | ← |
| 18 | ✓ | ← | ← | ← |
| 20 | ✓ | ← | ← | ← |
| 22 | ✓ | ← | ← | ← |
| 24 | | ✓ | ← | ← |
| 26 | | ✓ | ← | ← |
| 28 | | ✓ | ← | ← |
| 30 | | ✓ | ← | ← |
| 32 | | ✓ | ← | ← |
| 34 | | ✓ | ← | ← |
| 36 | | ✓ | ← | ← |
| 38 | | ✓ | ← | ← |
| 40 | | ✓ | ← | ← |
| 42 | | ✓ | ← | ← |
| 44 | | | ✓ | ← |
| 46 | | | ✓ | ← |
| 48 | | | ✓ | ← |
| 50 | | | ✓ | ← |
| 52 | | | ✓ | ← |
| 54 | | | ✓ | ← |
| 56 | | | ✓ | ← |
| 58 | | | ✓ | ← |
| 60 | | | ✓ | ← |
| 62 | | | ✓ | ← |
| 64 | | | | ✓ |
| 66 | | | | ✓ |
| 68 | | | | ✓ |
| 70 | | | | ✓ |
| 72 | | | | ✓ |
| 74 | | | | ✓ |
| 76 | | | | ✓ |
| 78 | | | | ✓ |
| 80 | | | | ✓ |

✓ GLP-1 Dose may be dialed and delivered
← Low dose - Cannot be dispensed
High dose - Cannot be dialed

FIG. 7

Table 3

| Dialed long acting Insulin Dose | Premix Pen Number | | | | | |
|---|---|---|---|---|---|---|
| | 1 | 2 | 3 | 4 | 5 | 6 |
| | Mix ratio (insulin:GLP-1) | | | | | |
| | 0.83 | 0.665 | 0.53 | 0.43 | 0.35 | 0.285 |
| 2 | | | | | | |
| 4 | | | | | | |
| 6 | | | | | | |
| 8 | | | | | | |
| 10 | | | | | | |
| 12 | | | | | | |
| 14 | | | | | | |
| 16 | | | | | | |
| 18 | | | | | | |
| 20 | | | | | | |
| 22 | 18.3 | | | | | |
| 24 | 19.9 | | | | | |
| 26 | 21.6 | | | | | |
| 28 | | 18.6 | | | | |
| 30 | | 20.0 | | | | |
| 32 | | 21.3 | | | | |
| 34 | | | 18.0 | | | |
| 36 | | | 19.1 | | | |
| 38 | | | 20.1 | | | |
| 40 | | | 21.2 | | | |
| 42 | | | | 18.1 | | |
| 44 | | | | 18.9 | | |
| 46 | | | | 19.8 | | |
| 48 | | | | 20.6 | | |
| 50 | | | | 21.5 | | |
| 52 | | | | | 18.2 | |
| 54 | | | | | 18.9 | |
| 56 | | | | | 19.6 | |
| 58 | | | | | 20.3 | |
| 60 | | | | | 21.0 | |
| 62 | | | | | 21.7 | |
| 64 | | | | | | 18.2 |
| 66 | | | | | | 18.8 |
| 68 | | | | | | 19.4 |
| 70 | | | | | | 20.0 |
| 72 | | | | | | 20.5 |
| 74 | | | | | | 21.1 |
| 76 | | | | | | 21.7 |
| 78 | | | | | | |
| 80 | | | | | | |

GLP-1 Dose may be dialed and delivered
Low dose - Cannot be dispensed
High dose - Cannot be dialed though they may not receive medical training. The device must be easy to understand in terms of how to administer the correct dose.

DOSE SETTING MECHANISM AND METHOD OF USING SAME

CROSS REFERENCE TO RELATED APPLICATIONS

The present application is a U.S. National Phase Application pursuant to 35 U.S.C. §371 of International Application No. PCT/EP2011/067677 filed Oct. 11, 2011, which claims priority to U.S. Provisional Patent Application No. 61/392,749 filed Oct. 13, 2010 and European Patent Application No. 11168189.6 filed May 31, 2011. The entire disclosure contents of these applications are herewith incorporated by reference into the present application.

FIELD OF DISCLOSURE

The present patent application is generally directed to dose setting mechanisms for drug delivery devices that control minimum and/or maximum possible dose settings and a method of using same, e.g. by setting and/or delivering at least a predetermined minimum dose of a medicament. More particularly, the present patent application is generally directed to drug delivery devices, such as pen type drug delivery devices where therapy demands that a patient receive at least a certain minimum dose and not exceed a certain maximum dose of a particular medicament. Such devices provide for self-administration of medicinal product from a multi-dose cartridge and contain dose limiting mechanisms for setting minimum and/or maximum doses. The present application may find application in both disposable and reusable type drug delivery devices. However, aspects of the invention may be equally applicable in other scenarios as well.

BACKGROUND

Self administered injectable medicaments are often delivered using a variable-dose injection device. Such a device is known from WO 2004/078239 A1. Prior to the injection the user selects the dose that they require according to their prescribed dose and/or their current or expected future physical condition. A typical example would be an insulin delivery device for diabetics where a patient's dose is determined according to their prescribed dose and their expected food intake and activity level. Typically such devices allow the user to select any dose from 1 unit up to the maximum units that the device can deliver, typically 60 units or 80 units for a manual device, such as a pen-type or syringe injection device.

The drug delivery device of WO 2004/078239 A1 comprises a housing for receiving a dose setting mechanism, a cartridge, a dose dial sleeve with an attached dose dial grip, a clicker, a drive sleeve, a clutch for coupling and decoupling the dose dial sleeve and the drive sleeve, a rotatable piston rod and a button which is pressed for injecting a set dose. The full description of the pen-type injection devices disclosed in WO 2004/078239 A1 is incorporated herein by reference.

To dial a dose a user rotates the dose dial grip. With the clicker and clutch means engaged, the drive sleeve, the clicker, the clutch means and the dose dial sleeve rotate with the dose dial grip relative to the housing and relative to the piston rod. Audible and tactile feedback of the dose being dialed is provided by the clicker and the clutch means. Torque is transmitted through saw teeth between the clicker and the clutch means.

A helical groove on the dose dial sleeve and a helical groove in the drive sleeve have the same lead. This allows the dose dial sleeve to extend from the housing and the drive sleeve to climb the piston rod at the same rate. At the limit of travel, a radial stop on the dose dial sleeve engages a stop provided on the housing to prevent further movement. Rotation of the piston rod is prevented due to the opposing directions of overhauled and driven threads on the piston rod.

Should a user inadvertently dial beyond the desired dosage, the pen-type injector allows the dosage to be dialed down without dispense of medicinal product from the cartridge. The dose dial grip is counter rotated. This causes the system to act in reverse. The torque transmitted through the clutch means causes the saw teeth to ride over one another to create the clicks corresponding to dialed dose reduction. Preferably the saw teeth are so disposed that the circumferential extent of each saw tooth corresponds to a unit dose.

When the desired dose has been dialed, the user may then dispense this dose by depressing the button. This displaces the clutch means axially with respect to the dose dial sleeve causing dog teeth of the clutch means to disengage. However the clutch means remains keyed in rotation to the drive sleeve. The dose dial sleeve and associated dose dial grip are now free to rotate. The axial movement deforms a flexible part of the clicker to ensure the saw teeth cannot be overhauled during dispense. This prevents the drive sleeve from rotating with respect to the housing though it is still free to move axially with respect thereto. This deformation is subsequently used to urge the clicker and the clutch back along the drive sleeve to restore the connection between the clutch and the dose dial sleeve when pressure is removed from the button. The longitudinal axial movement of the drive sleeve causes the threaded piston rod to rotate through a threaded opening in a housing insert, thereby to advance the piston in the cartridge.

In other words, the drive sleeve moves longitudinally, i.e. only in the axial direction, during an injection. Because the drive sleeve and the piston rod are engaged via corresponding threads on the outer surface of the piston rod and an internal face of the drive sleeve, the longitudinal movement of the drive sleeve causes the piston rod to rotate. The housing insert with the threaded opening which is engaged with the piston rod via corresponding threads is fixed within the housing, i.e. prevented from rotation. Thus, the rotating piston rod is screwed through the threaded opening in the housing insert, i.e. the piston rod performs a combined rotational and longitudinal movement along a helical path defined by the corresponding threads of the threaded opening and the piston rod.

Once the dialed dose has been dispensed, the dose dial sleeve is prevented from further rotation by contact of a plurality of members extending from the dose dial grip with a corresponding plurality of stops formed in the housing, thus determining a zero dose position.

Such pen type drug delivery devices have been designed and developed to perform regular injections by persons without formal medical training. This is increasingly common among patients having diabetes where self-treatment enables such patients to conduct effective management of their disease. Because the patient, and not the health care worker, may be using such a drug delivery device, one requirement is that the device should be robust in construction. The drug delivery device must also be easy to use both in terms of the drug delivery device manipulation and understanding of the device's operation. This is especially true for diabetics who are required to inject themselves repeatedly with insulin solution and the volume of insulin to be injected may vary from patient to patient and even from injection to injection. For at least this reason, certain diabetics may require drug delivery devices that allow the patient to inject successive measured dosages of the same or perhaps different preset volumes of insulin solution accurately and with minimum dexterity challenges. This presents a further design challenge since, in the case of certain diabetics, users may have impaired vision and/or may be physically infirm with limited dexterity.

In addition to insulin, other medicaments require a minimum dose to be delivered before they are therapeutically effective. A variable-dose device that allows the patient to deliver doses below the therapeutically effective minimum dose creates the possibility that the user may deliver the ineffective doses either by an error of dose calculation or by mistakenly selecting the incorrect dose. Likewise, some medicaments require that a maximum dose is not to be exceeded. This may be for safety reasons such as increased risk or severity of side-effects or excessive or unwanted actions of the medicament. Current variable-dose delivery devices typically have a maximum dose that is limited by the maximum dose that the delivery mechanism can provide, however, this does not necessarily relate to the maximum advised or prescribed dose of the medicament.

SUMMARY

The present invention has at least two applications. First, is the delivery of a single active medicament which must be a variable dose within a defined dose window, i.e. the dose must be more than a certain minimum dose and must not exceed a certain maximum dose. The second application relates to the delivery of a combined formulation of active medicaments where at least one of the medicaments is preferably delivered as a variable dose and at least one other medicament is preferably delivered as a fixed dose, and where this fixed dose can safely be allowed to vary within a defined dose window, for example by ±10% of the nominal fixed dose.

The minimum and/or maximum dose limited delivery device in accordance with the present invention could be used for a medicament that requires a minimum dose to be delivered before it becomes therapeutically effective, but where a degree of dose adjustment may be required. This dose adjustment may be required for a number of reasons, including tailoring a dose to a patient's body weight or the severity of their medical condition. The minimum and maximum dose limited device (min/max device) may also be used instead of a fully variable (i.e., 0 to max dose) device in order to reduce the possibility for dosing errors by the patient. Using the min/max device rather than a variable dose pen reduces the risk that a patient might accidentally deliver a dose outside the defined dose window, i.e., either too high or too low.

One example of the utility of the min/max device is where a parent could give the min/max delivery device to a child for the child to self-administer and the parent would know that the minimum and maximum levels of the min/max device limited the possible severity of any overdose or under dose. Another example of where such a device might be applicable is for patients who take long acting insulin. Typically a variable dose pen is required when a patient is "titrating" their dose to reach their target blood glucose level. However, once the target blood glucose level has been achieved the dose of long acting insulin typically remains more or less constant over relatively long periods of time. During this period, where their insulin dose is either constant or changes by only a few units on a day-to-day basis, the patient's long acting insulin needs could be effectively met by the minimum and maximum dose limited delivery device.

Table 1 (provided below) shows an example family of delivery devices, "Pen 1" through "Pen 4", which could be used in place of a single 1-80 unit variable dose device. Each of the Pens 1-4 are designed and manufactured around the same basic mechanism, but each pen contains either additional or alternative components which are used to set a different minimum and maximum dose. Patients would be prescribed a particular Pen according to their stable long acting insulin dose. For example, according to Table 1 a patient prescribed 30 units per day of long acting insulin would be prescribed Pen 2, which has a minimum dose of 18 units and a maximum dose of 42 units, respectively. Any number of mechanical components can be used in such a pen design to ensure these predetermined min/max doses, including axial and/or rotational stops, detents, clutches, compressible fingers, or the like components.

The insulin dose of diabetic patients may change gradually over time. Therefore there may be a small amount of dose range overlap between Pens to allow for a smooth transition between Pens as the dose increases. For example, according to Table 1 a patient prescribed 40 units per day of long acting insulin would be given Pen 2 if they expected their dose to decrease over time or Pen 3 if they expected their dose to increase over time. The number of pens in the "family" and the selected dose ranges shown in Table 1 are illustrative only. By using the min/max device of the present invention a mistake when selecting the dose is limited to within the pen's operating window. Dialing a dose above or delivering a dose below the pen's dose range would not be possible and this would alert the patient to their error.

The min/max device may also be applicable for the delivery of other medicines, particularly where there is a risk of confusion with similar devices that may lead to dose errors or drug/device mix-ups. One such example would be rapid acting insulin and long acting insulin. Both of these insulins are measured in "units" however the same number of units of each insulin type will have a very different effect and a patient will be prescribed different doses of each drug to be taken at different times throughout the day. A mix up of long acting and rapid acting insulin can cause hypoglycemia and is potentially fatal. Both types of insulin may be delivered by injection pen devices. Patients perform their injections on such a routine basis that an "automatic pilot" effect can occur where patients have been known to mix up their insulin pens, even though the pens are of different design, color, shape and carry different labels.

The presently proposed min/max device may help to prevent this mix up occurring. For example, assume both rapid acting and long acting insulins were each provided with a family of min/max devices according to Table 1. A patient is prescribed 50 units per day of long acting insulin (which would require long acting Pen 3) and 15 units of rapid acting insulin with meals (which would require Pen 1). The most dangerous mix up would occur if the patient mistakenly delivered 50 units of rapid acting insulin rather than long acting insulin. If the patient attempted to do this with the min/max devices then the patient would pick up the rapid insulin device (Pen 1) and find that they could not dial beyond 22 units. This should alert them to the fact that this is not the correct insulin pen, and therefore the incorrect insulin type, and prevent the incorrect insulin being delivered.

The min/max concepts may be applied equally to both disposable devices and reusable devices.

Certain medicines also require the user to perform a "priming" dose to confirm the correct operation of the delivery device and needle. This is usually accomplished by delivering an "air-shot" of 2 units and then checking that the medicine can be seen coming out of the needle. The min/max concept shown in Table 1 would not permit this. If priming functionality is required a second permissible "dose window", for example ranging from 1-2 units, may also be implemented within each pen mechanism. An example of how this could be applied is shown in Table 2. Although both Tables 1 and 2 show only even numbers of units this is done only for clarity and the device may be configured to deliver odd and even units or potential ½ units.

As mentioned, the presently disclosed devices may also be useful in therapies where the delivery of a combined formulation of active medicaments is needed, where at least one of the medicaments is preferably delivered as a variable dose and at least one other medicament is preferably delivered as a fixed dose. If a patient requires a combination of medicines then there is an advantage if those medicines can be provided as a single formulation (i.e. both drugs are mixed together in predefined proportions and supplied in one primary pack) for delivery by a single injection device in one injection through a single needle. However, if one of the drugs requires the delivery of a user-selectable variable dose and the second drug requires a dose above a minimum dose to be therapeutically effective and must not exceed a given maximum dose, then it is beneficial for the drug delivery device to be configured such that it is prevented from delivering doses that are outside of this range.

For example, a patient may be prescribed a combination therapy of long acting insulin (typically delivered in variable dose devices) and GLP-1 (typically delivered as a fixed dose). GLP-1 is a glucagon-like peptide-1, which is derived from the transcription product of the proglucagon gene and is found in the body where it is secreted by the intestinal L cell as a gut hormone. GLP-1 possesses several physiological properties that make it (and its analogs) a subject of intensive investigation as a potential treatment of diabetes mellitus. In order to avoid the patient having to perform two injections the two medicines are pre-mixed into a single formulation. Since both medicaments are pre-mixed in a fixed ratio it is not possible to vary the long acting insulin dose without also varying the GLP-1 dose. However, it may be acceptable for the GLP-1 dose to vary within a given tolerance, for example ±10%, around a fixed nominal dose. It is therefore possible, using a family of min/max limited devices to provide a family of pre-mix devices which between them will allow delivery of a variable long acting insulin dose and a GLP-1 dose that always falls within ±10% of a given "fixed" dose.

Table 3, for example, shows a family of 6 min/max pen-type injection devices that allow the delivery of any long acting insulin dose from 22-76 units along with a GLP-1 dose that is "fixed" to 20 mg±10%. Each Pen within the family would have different minimum and maximum dose thresholds and would be provided with a primary pack or cartridge of medicament filled with the appropriate mix ratio of the two medicines. The family of pen devices could be provided as disposable mechanical devices, prefilled with the appropriate mix ratio cartridge of medicament. Alternatively, the family of devices could be provided as reusable mechanical devices. In the latter case, the devices would be preferably dedicated to a particular mix ratio cartridge, i.e. only the correct mix ratio cartridge can be loaded into each pen family member.

A third alternative is to provide the "family" of pen devices via a single electronic device that can be programmed with the minimum and maximum dose functionality. Preferably, the min/max electronic device would be loaded with a coded cartridge that would automatically upon being loaded into the device communicate to the device what the required minimum and maximum thresholds should be for that particular cartridge and mix ratio.

One specific means of achieving a minimum settable dose on a variable dose, drug delivery device, such as a pen-type device, is to include a mechanism that prevents dosing of the device until a predetermined minimum dose has been reached. A maximum dose mechanism can also be used with a minimum dose mechanism.

It is an object of the invention to provide a device that reduces or eliminates the risk that a user of an injection device will set and administer a dose below a preselected minimum effective dose of a particular medicament.

This object is solved with a dose setting mechanism as defined in claim 1 and methods as defined in claims 11 and 12.

According to one possible exemplary embodiment of the present invention a dose setting mechanism for a drug delivery device is provided comprising a drug delivery device housing, a dose dial sleeve provided at least partly in the housing and rotatable during dose setting and dose delivery, a clutch rotatable during dose setting and non-rotatable during dose delivery, and a clutch nut having a proximal end and a distal end, wherein the proximal end is threadedly engaged with the clutch and the distal end is splined to the housing to prevent rotation of the clutch nut. Preferably, the clutch nut is releasably coupled to the dose dial sleeve such that a relative rotation between the clutch nut and the dose dial sleeve is prevented in at least one rotational direction. More specifically, the clutch nut may be fixed to the dose dial sleeve from a dose of 0 to a predetermined minimum dose and/or from a dose above a predetermined maximum dose by means of interacting splines or by means of a one-directional coupling or ratchet. For a drug delivery device like the one disclosed in WO 2004/078239 A1, the clutch nut may be in ratchet engagement with the dose dial sleeve to allow the dose dial sleeve to rotate in only a single direction and preventing rotation in the opposite direction.

If the clutch nut is threadedly engaged with the clutch through flexible fingers, the clutch nut may be moved relative to the clutch allowing the respective threads to snap or ride over each other.

The clutch nut is preferably splined to the dose dial sleeve when the user sets a dose from 0 to a predetermined minimum dose. When at least a predetermined dose is set, then pressing a dose button on the injection device causes the clutch nut to fully disengage from the dose dial sleeve. However, if the user sets a dose less than the predetermined minimum then the dose dial sleeve remains engaged with the clutch nut and is non-rotatable and locked from movement in a distal direction because the dose dial sleeve is in threaded engagement with the housing and thus may only move in an axial direction by rotational movement on a helical path defined by the respective threads.

As an alternative or in addition to preventing a user from delivering a too small dose of medicament, a maximum dose mechanism may be provided preventing a user from delivering a dose exceeding a predefined maximum dose.

According to the present invention, this may be achieved in the same way as described above using a clutch nut provided between the dose dial sleeve and the clutch.

Further, the present invention also relates to one or more methods of preventing a user from delivering too small a dose of medicament. One such method involves delivering at least a predetermined minimum dose of a medicament comprising rotating a dose dial sleeve in a first direction relative to a device housing during dose setting, wherein the dose dial sleeve is in ratchet engagement with a clutch nut, preventing rotation of the clutch nut relative to the housing and preventing rotation of the dose dial sleeve in a second direction opposite the first direction by means of the clutch nut when a dose of from 0 to less than a predetermined minimum dose and/or a dose above a predetermined maximum dose is set.

Another possible method of delivering at least a predetermined minimum dose of a medicament comprises rotating a dose dial sleeve in a first direction relative to a device housing, where the dose dial sleeve is in ratchet engagement with a clutch nut, moving the clutch nut in an axial distal direction relative to the dose dial sleeve during dose setting, disengaging the clutch nut from the dose dial sleeve when a dose above a predetermined minimum dose has been set, and pushing a dose button to deliver the dose. To prevent setting a dose higher than a predetermined maximum dose, the method involves moving the clutch nut which is disengaged from the dose dial sleeve if a dose below a predetermined maximum dose has been set in an axial proximal direction relative to the dose dial sleeve during dose setting, and engaging the clutch nut with the dose dial sleeve as soon as the predetermined maximum dose has been set.

These as well as other advantages of various aspects of our proposed drug delivery device will become apparent to those of ordinary skill in the art by reading the following detailed description, with appropriate reference to the accompanying drawings.

BRIEF DESCRIPTION OF THE FIGURES

Exemplary embodiments are described herein with reference to the drawings, in which.

DETAILED DESCRIPTION

Figure 1:
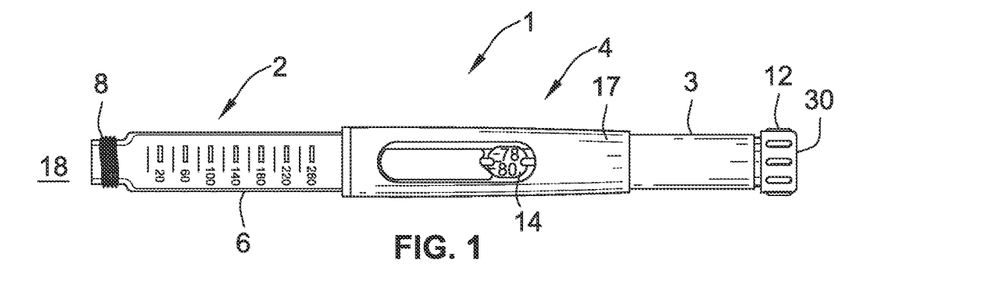
FIG. 1 illustrates a generic design of a pen-type drug delivery device capable of accepting the min/max functionality of the present invention.

Referring to FIG. 1, there is shown a drug delivery device 1 in accordance with an exemplary pen-type design arrangement. The drug delivery device 1 comprises a housing having a body 17 and a first cartridge retaining part 2, and a dose setting mechanism 4. The drug delivery device may be a resettable drug delivery device (i.e., a reusable device) or alternatively a non-resettable drug delivery device (i.e., a non-reusable device). A first end of the cartridge retaining part 2 and a second end of the dose setting mechanism 4 are secured together by connecting features. For non-resettable devices, these connecting features would be permanent and non-reversible. For resettable devices, these connecting features would be releasable.

In this illustrated arrangement, the cartridge retaining part 2 is secured within the second end of the dose setting mechanism 4. A removable cap (not shown) is releasably retained over a second end or distal end of a cartridge retaining part or cartridge housing. The dose setting mechanism 4 comprises a dose dial grip 12 and a window or lens 14. A dose scale arrangement 3 provided on a dose dial sleeve 9 is viewable through the window or lens 14. To set a dose of medication contained within the drug delivery device 1, a user rotates the dose dial grip 12 such that a dialed dose will become viewable in the window or lens 14 by way of the dose scale arrangement.

FIG. 1 illustrates the medical delivery device 1 with the cover cap removed from a distal end 18 of the medical delivery device 1. This removal exposes the cartridge housing 6 of cartridge retaining part 2. Preferably, a cartridge (not shown) from which a number of doses of a medicinal product may be dispensed, is provided in the cartridge housing 6. Preferably, the cartridge contains a type of medicament that can be administered relatively often, such as once or more times a day. One such medicament is either long acting or short acting insulin or an insulin analog. The cartridge comprises a bung or stopper that is retained near a second end or a proximal end of the cartridge. The medical delivery device also comprises a driver 7 engaged with a spindle (not illustrated in FIG. 1, but is illustrated as item 5 in FIG. 2). The driver 7 is preferably threadedly engaged to a spindle or piston rod 5. Also part of the drive mechanism, which generally includes the dose dial sleeve 9, driver 7, piston rod 5, is a clutch 13 or other release mechanism (not shown) that directly or indirectly, releasably couples the dose dial sleeve 9 to the driver 7. Preferably, the driver is coupled to the dose dial sleeve during dose setting and uncoupled during dose delivery. As discussed above, before the device is primed, there may or may not be a gap between the end of the spindle and the cartridge bung.

The cartridge housing 6 has a distal end 18 and a proximal end. Preferably, the distal end of the cartridge housing 6 comprises a hub 8 for attaching a removable needle assembly. However, other needle assembly connection mechanisms could also be used. If the drug delivery device 1 comprises a resettable device, the cartridge proximal end is removably connected to the dose setting mechanism 4. In one preferred embodiment, cartridge housing proximal end is removably connected to the dose setting mechanism 4 via a bayonet connection. However, as those of ordinary skill in the art will recognize, other types of removable connection methods such as threads, partial threads, ramps and detents, snap locks, snap fits, and luer locks may also be used.

As previously mentioned, the dose setting mechanism 4 of the drug delivery device illustrated in FIG. 1 may be utilized as a reusable drug delivery device. (i.e., a drug delivery device that can be reset) Where the drug delivery device 1 comprises a reusable drug delivery device, the cartridge is removable from the cartridge housing 6. The cartridge may be removed from the device 1 without destroying the device 1 by merely having the user disconnect the dose setting mechanism 4 from the cartridge housing 6.

In use, once the cap is removed, a user can attach a suitable needle assembly to the hub 8 provided at the distal end of the cartridge housing 6. Such needle assembly may be, for example, screwed onto a distal end 18 of the housing 6 or alternatively may be snapped onto this distal end. After use, the replaceable cap may be used to re-cover the cartridge housing 6. Preferably, the outer dimensions of the replaceable cap are similar or identical to the outer dimensions of the dose setting mechanism 4 so as to provide an impression of a unitary whole when the replaceable cap is in position covering the cartridge housing 6 when the device is not in use.

Figure 2:
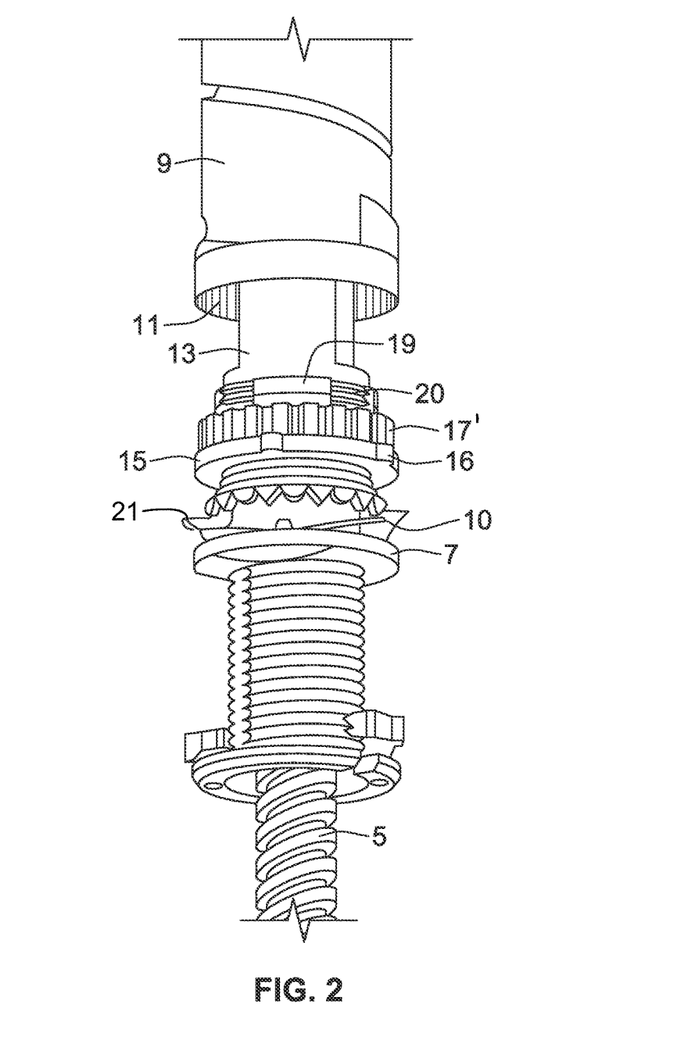
FIG. 2 illustrates a sectional view of a drug delivery device showing one possible embodiment of the dose setting mechanism of the present invention.

FIG. 2 shows one possible embodiment of the dose setting mechanism of the present invention that could be incorporated into the pen-type injection device illustrated in FIG. 1. The dose setting mechanism comprises a clutch nut 15, which is threadedly engaged at its proximal end with the distal end of a clutch 13. Clutch nut 15 is also engaged with dose dial sleeve 9 through an internal ratchet 11 located on the inside of dose dial sleeve 9. Also shown is a clicker spring 10, a drive member 7 and a spindle or lead screw 5. The clutch nut 15 has keying features 16, which run in axial splines in the body 17 of the device (not shown) and prevent the clutch nut from rotational movement during both dose setting and dose delivery. In addition, clutch nut 15 has spline features 17' that engage with the ratchet features 11 inside dose dial sleeve 9. The clutch nut 15 has threaded fingers 19 that engage with threads 20 on the clutch 13. The clicker spring 10 also has keying features 21, which run in the same axial splines in the body of the device as keying features 16 on the clutch nut.

During operation of the exemplified pen-type injection device containing the dose setting mechanism of the present invention device, the clutch nut 15 travels along the threads 20 on the clutch 13. The design of the threaded interface is such that the clockwise (CW) rotation of the clutch 15, which rotates with dose dial sleeve 9 during dose setting, causes the clutch nut to travel axially away (i.e. in the distal direction) from the dose dial sleeve 9. The threaded fingers 19 on the clutch nut are flexible such that, at the end of dose delivery, they can snap back over the threads 20 on the clutch 13, thus resetting the device for the next dose setting/dose delivery sequence.

As mentioned, the clutch nut 15 has splines 17' that engage ratchet 11 located on the inside circumference of dose dial sleeve 9. The combination of splines 17' and ratchet 11 allow clockwise rotation of the dose dial sleeve 9, driver 7, and clutch 13 during dose setting with respect the clutch nut 15, but do not allow counter-clockwise (CCW) rotation (i.e., during dispensing) of the dial sleeve 9 with respect to the clutch nut 15 unless they are axially disengaged from each other. Of course, the present invention is also applicable to an injection device design to operate in the reverse direction, i.e. one where the dose is set by rotating the dose dial sleeve in the counter-clockwise direction. Axial disengagement of the clutch nut 15 and the dose dial sleeve 9 allows the dose setting mechanism to achieve the minimum dose functionality.

When the dose dial sleeve 9 and clutch 13 have been wound out during dose setting to a predetermined minimum dose threshold, the clutch nut 15 will have advanced axially in the distal direction sufficiently along the clutch 13 to allow axial separation of the clutch nut splines 17' from ratchet teeth 11 inside dose dial sleeve 9. This axial separation allows counter-clockwise rotation of the dose dial sleeve back into the body of the device during dose delivery when dose button 30 is pushed. Dose delivery also causes axial travel of the driver 7 that allows the lead screw 5 to be overhauled and the drug compound(s) dispensed.

Figure 3:
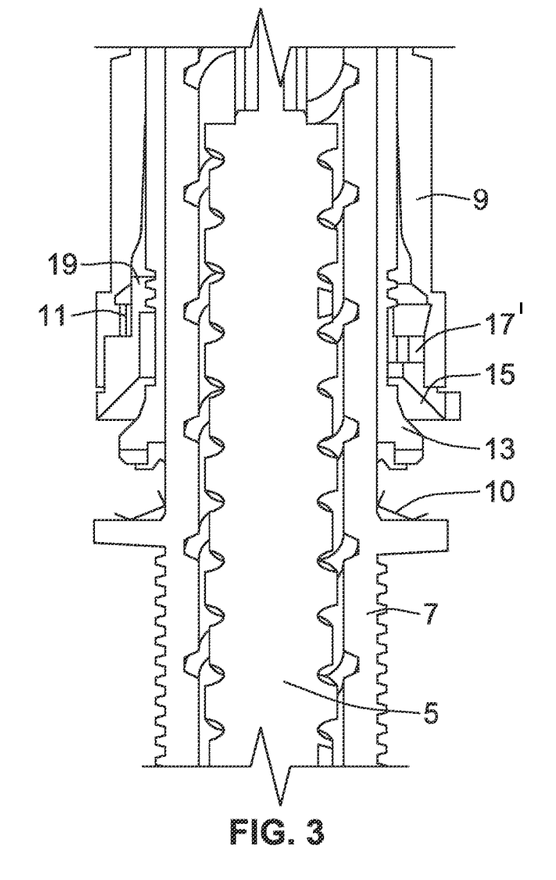
FIG. 3 illustrates the operation the drug delivery device of FIG. 2 in a cross-sectional view.

At the start of the dose setting procedure, the clutch nut 15 is in threaded engagement with the clutch 13. On dialling up (ie. setting the dose), rotation of the clutch 13 forces the clutch nut to move away (axially, i.e. distally) from the dose dial sleeve 9, thus reducing the amount of axial engagement between the clutch nut 15 and the dose dial sleeve 9. The amount of axial disengagement is proportional to the number of rotations of the dose dial sleeve 9 and clutch 13, and the pitch of the engagement threads 20 between the clutch 13 and the clutch nut 15. Once a sufficient axial disengagement occurs at the predetermined minimum dose setting then the dose dial sleeve will no longer be locked from rotational movement back into the device body during dispensing. Below the minimum dose threshold, the splines 17' remain engaged with the ratchet features 11 in the dose dial sleeve 9. This is shown in FIG. 3. Because keying features 16 prevent clutch nut 15 from rotating with respect to the body 17, this also prevents dose dial sleeve 9 from rotating, thus locking the device from dose delivery.

Figure 4:
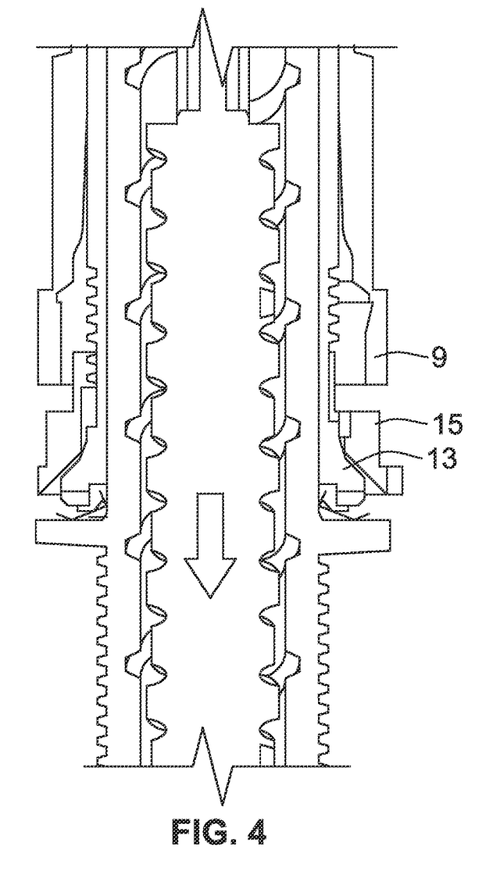
FIG. 4 illustrates a cross-sectional view of the dose mechanism of the drug delivery device of FIG. 2 having a mechanism to force setting of a minimum predetermined dose.
Figure 5:
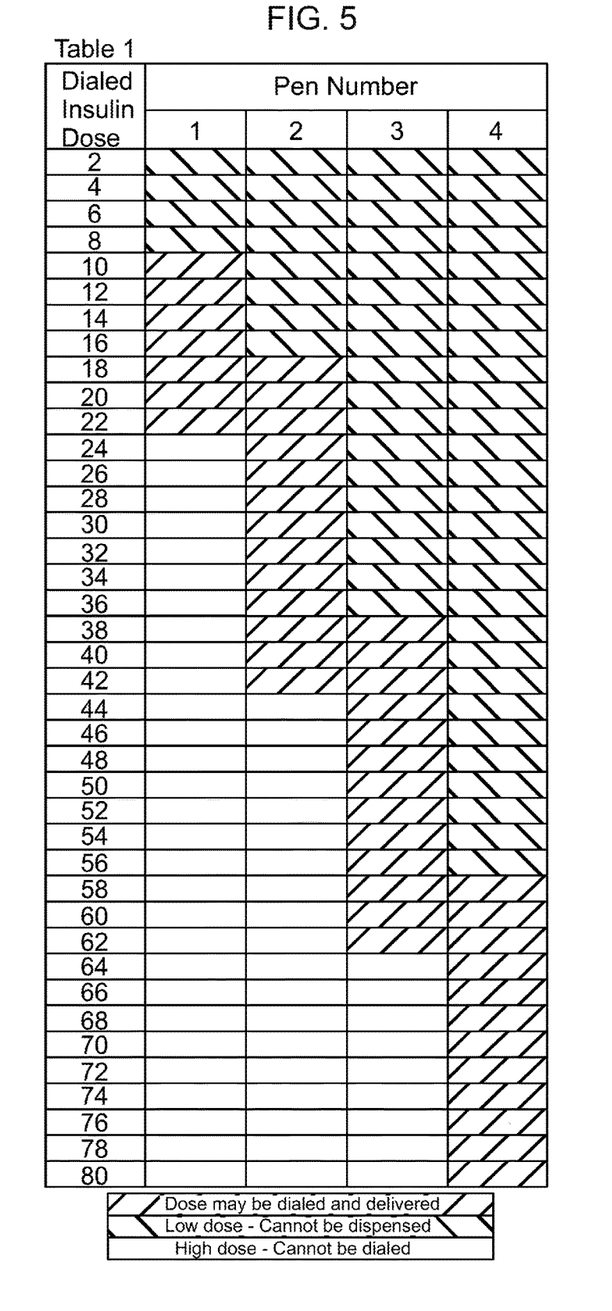
FIG. 5 illustrates a table of exemplary dosing regime using a family of delvery devices designated as Pen 1-Pen 4.
Figure 6:
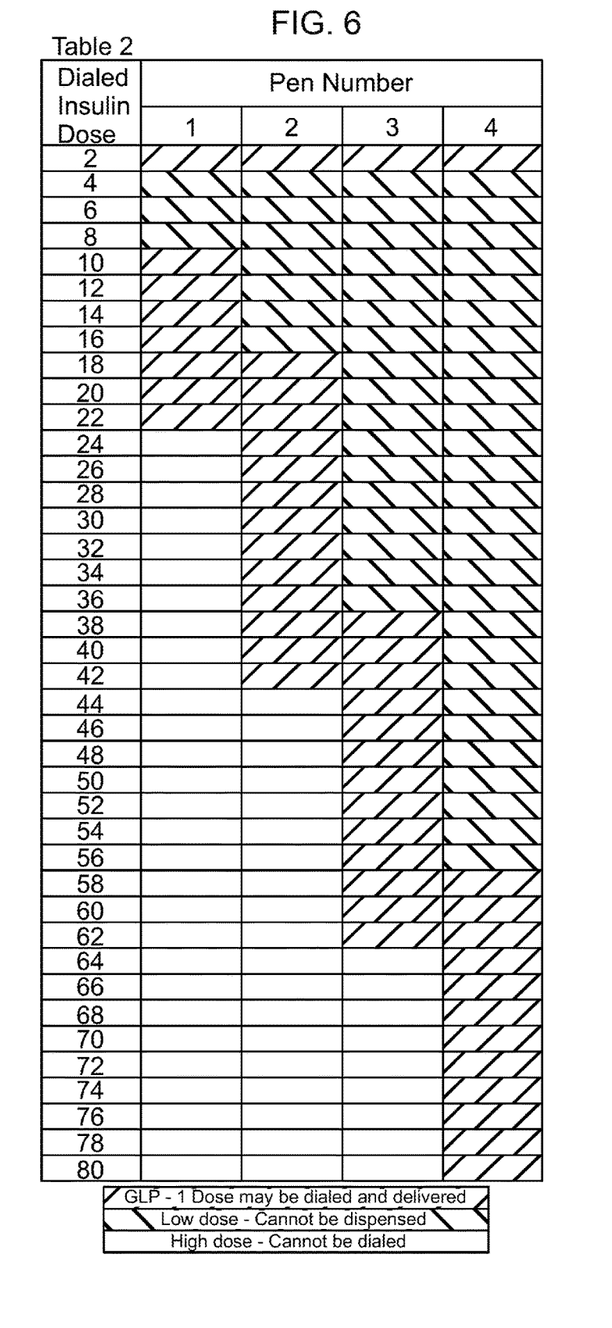
FIG. 6 illustrates a table of another exemplary dosing regime using a family of delvery devices designated as Pen 1-Pen 4.
Figure 7:
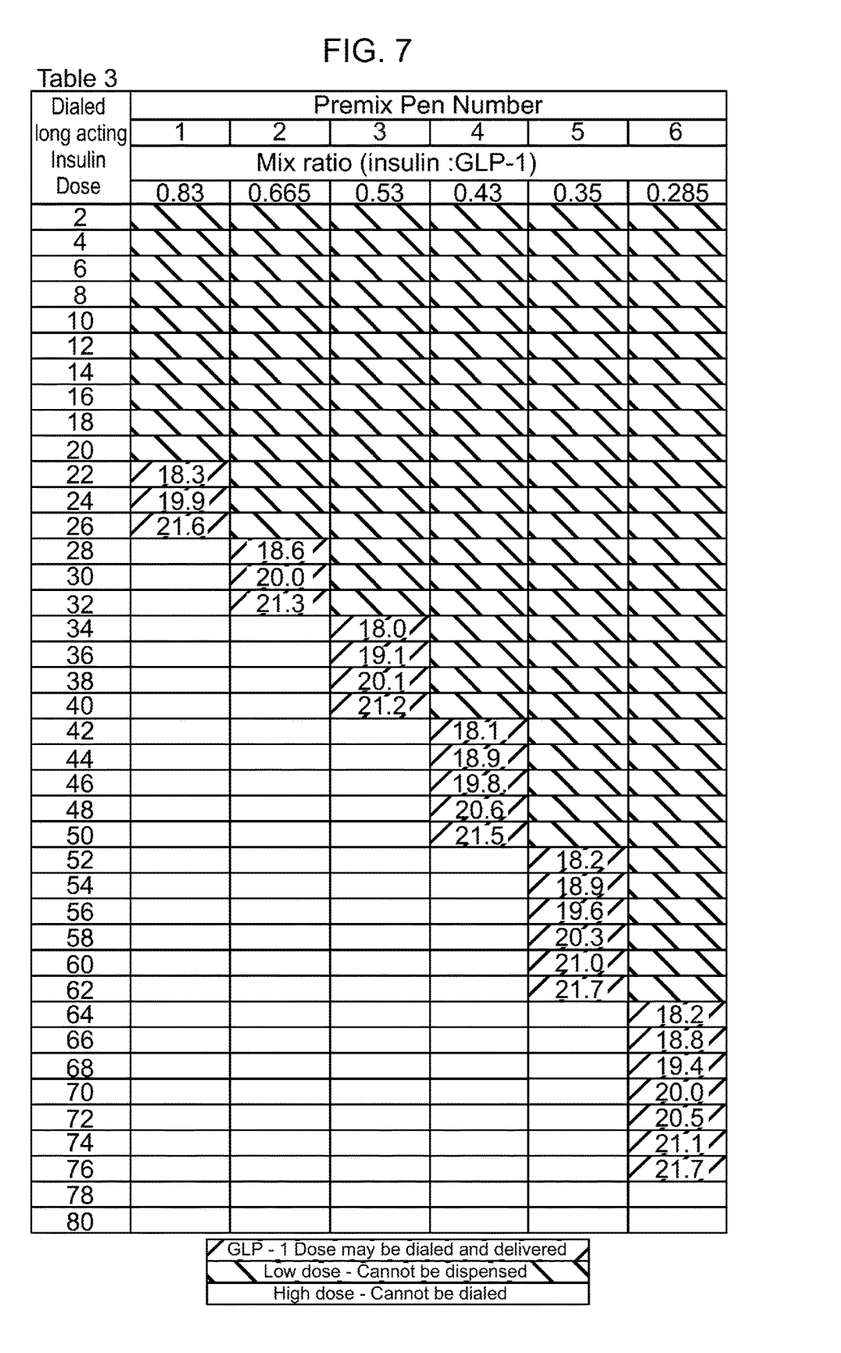
FIG. 7 illustrates a table of yet another exemplary dosing regime using a family of delvery devices designated as Pen 1-Pen 6.

When the user presses the dose button 30 this forces the clutch 13 and clutch nut 15 axially in a distal direction. If the device has passed the predetermined minimum dose limit, the clutch nut will have advanced sufficiently along the clutch such that, with the combined downward travel of the clutch under the action of the dose button, causing the spline features 17' on the clutch nut to disengage from the ratchet features 11 on the dose dial sleeve 9 if this has not already occurred due to setting a higher dose. Once disengaged, as shown in FIG. 4, the dose dial sleeve can rotate freely back into the body of the device thus allowing dose dispensing. If the device has not reached the predetermined minimum dose threshold then the clutch nut will not have advanced sufficiently far along the clutch to allow for the disengagement of the spline features from the ratchet features. This means that the dose dial sleeve cannot rotate back into the body 17 of the device and thus the device is locked up and does not allow the user to dispense a dose.

The device is reset to its initial "locked" condition or beginning of the dose setting sequence, when, at the end of dose delivery, the keying features 16 on the clutch nut reach the end of the body splines. When the keying features 16 reach the bottom of the body splines they are prevented from further travel with respect to the body 17 and as a result the clutch nut is forced in an axially proximal direction with respect to the clutch 13 and the flexible fingers 19 snap over the threads 20 on the clutch 13 thus resetting the device.

An added benefit of the dose setting mechanism is that by altering the pitch of the threads 20 and/or the length of the threaded interface between the clutch 13 and the clutch nut 15, the predetermined minimum dose threshold may be altered. This design feature, in conjunction with a maximum dose limit, means that a range of therapeutically effective dose windows may be created thus tailoring the dose regime to meet the needs of a specific therapy.

As an alternative to the device depicted in FIGS. 2 to 4, a maximum dose limit may be provided by changing the thread lead such that the clutch nut 15 is out of engagement with the dose dial sleeve at the beginning of dose setting and approaches same during dose setting. As soon as a predetermined maximum dose is reached, the interaction of the clutch nut and the dose dial sleeve prevents either a further dose setting and/or prevents dispensing a dose exceeding the predetermined maximum dose.

In a preferred embodiment a master drug compound, such as insulin, contained within a multiple dose, user selectable device could be used with a single use, user replaceable, module that contains a single dose of a secondary medicament and the single dispense interface. When connected to the primary device, the secondary compound is activated/delivered on dispense of the primary compound. Although the present application specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with our invention.

For the purposes of our invention the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys(B3), Glu(B29) human insulin; Lys(B28), Pro (B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH2).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

Exemplary embodiments of the present drug delivery device have been described. Those skilled in the art will understand, however, that changes and modifications may be made to these embodiments without departing from the true scope and spirit of the presently proposed drug delivery device, which is defined by the claims.

The invention claimed is:

1. A dose setting mechanism for a drug delivery device, the mechanism comprising:
   a drug delivery device housing;
   a dose dial sleeve positioned at least partly in the housing and is rotatable during dose setting and dose delivery,
   a clutch rotatable during dose setting and non-rotatable during dose delivery; and
   a clutch nut, that is threadedly engaged with the clutch and is splined to the housing to prevent rotation of the clutch nut,
   wherein the clutch nut is fixed to the dose dial sleeve from a dose of 0 to a predetermined minimum dose by means of interacting splines or by means of a one-directional coupling or ratchet and is disengaged from the dose dial sleeve when a dose greater than the predetermined minimum dose is set,
   wherein the dose dial sleeve is non-rotatable and locked from movement in a distal direction during attempted dose delivery if the set dose is from 0 to less than a predetermined minimum dose.

2. The mechanism of claim 1, wherein the clutch nut is releasably coupled to the dose dial sleeve such that a relative rotation between the clutch nut and the dose dial sleeve is prevented in at least one rotational direction.

3. The mechanism of claim 1, wherein the clutch nut is in ratchet engagement with the dose dial sleeve to allow the dose dial sleeve to rotate in only a single direction.

4. The mechanism of claim 1, wherein the clutch nut is fixed to the dose dial sleeve from a dose larger than a predetermined maximum dose by means of interacting splines or by means of a one-directional coupling or ratchet.

5. The mechanism of claim 1, wherein the clutch nut is threadedly engaged with the clutch through flexible fingers.

6. The mechanism of claim 1 further comprising a dose button for initiating and/or executing injection of a set dose, wherein when the dose button is pushed the clutch nut is not engaged with the dose dial sleeve when a dose greater than the predetermined minimum dose has been set.

7. The mechanism of claim 1 further comprising a dose button for initiating and/or executing injection of a set dose, wherein when the dose button is pushed the clutch nut is not engaged with the dose dial sleeve when a dose smaller than the predetermined maximum dose has been set.

8. The mechanism of claim 1, wherein the dose dial sleeve is non-rotatable and locked from movement in a distal direction during attempted dose delivery if the set dose is above a predetermined maximum dose.

9. A method of delivering at least a predetermined minimum dose of a medicament from a drug delivery device comprising
   rotating a dose dial sleeve in a first direction relative to a device housing, where the dose dial sleeve is in ratchet engagement with a clutch nut such that there is no relative rotation between the dose dial sleeve and the clutch nut in a second direction opposite the first direction when a dose of from 0 to less than a predetermined minimum dose set;
   preventing rotation of the clutch nut relative to the housing; and
   allowing rotation of the dose dial sleeve in the second direction when a dose above a predetermined maximum dose is set causing the ratchet engagement between the clutch nut and dose dial sleeve to disengage.

10. A method of delivering at least a predetermined minimum dose of a medicament from a drug delivery device comprising rotating a dose dial sleeve in a first direction relative to a device housing, where the dose dial sleeve is in ratchet engagement with a clutch nut, where rotation in the first direction causes the dose dial sleeve wind outwardly relative to the housing and the clutch nut;
moving the clutch nut in an axial distal direction relative to and opposite to the winding outward of the dose dial sleeve during dose setting;
disengaging the clutch nut from the dose dial sleeve when a dose above a predetermined minimum dose and has been set; and
pushing a dose button to deliver the dose.

* * * * *